US012254062B2

(12) United States Patent
Yu et al.

(10) Patent No.: US 12,254,062 B2
(45) Date of Patent: Mar. 18, 2025

(54) DOMAIN ADAPTATION

(71) Applicant: International Business Machines Corporation, Armonk, NY (US)

(72) Inventors: Yi Qin Yu, Beijing (CN); Shiwan Zhao, Beijing (CN); Jing Mei, Beijing (CN); Shao Chun Li, Beijing (CN); Xu Min, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1240 days.

(21) Appl. No.: 17/003,104

(22) Filed: Aug. 26, 2020

(65) Prior Publication Data
US 2022/0067433 A1    Mar. 3, 2022

(51) Int. Cl.
*G06N 20/00* (2019.01)
*G06F 18/214* (2023.01)
*G06F 18/22* (2023.01)
*G06F 18/2431* (2023.01)
(Continued)

(52) U.S. Cl.
CPC ............ *G06F 18/214* (2023.01); *G06F 18/22* (2023.01); *G06F 18/2431* (2023.01); *G06N 3/08* (2013.01); *G06N 20/00* (2019.01); *G16H 10/60* (2018.01)

(58) Field of Classification Search
CPC ........ G06N 20/00; G06N 3/08; G06N 3/0895; G06N 3/09; G06N 3/091; G06N 3/092; G06N 3/094; G06N 3/096; G06N 3/098; G06N 3/0985
See application file for complete search history.

(56) References Cited

U.S. PATENT DOCUMENTS

| 11,164,108 B2* | 11/2021 | Desai | G06F 16/285 |
| 2015/0310263 A1* | 10/2015 | Zhang | H04N 23/51 |
| | | | 382/103 |
| 2018/0089152 A1* | 3/2018 | Maksak | G06F 40/30 |

(Continued)

FOREIGN PATENT DOCUMENTS

| CN | 110390950 A | 10/2019 |
| WO | 2018169639 A1 | 9/2018 |

OTHER PUBLICATIONS

Wang et al., "Private Model Compressing via Knowledge Distillation", 2019, The Thrity-Third AAAI Conference on Artificial Intelligence, pp. 1190-1198 (Year: 2019).*

(Continued)

*Primary Examiner* — Paulinho E Smith
(74) *Attorney, Agent, or Firm* — Rakesh Roy

(57) ABSTRACT

Embodiments of the present disclosure relate to a method, system, and computer program product for domain adaptation. According to the method, a source model of a source domain is obtained, where the source model is trained to generate a label indicating a predicted category of data from the source domain. A training sample from a target domain is obtained, where the training sample comprises training data from the target domain and a true label indicating a true category of the training data from the target domain. A first label is generated for the training data by using the source model. The first label indicates a predicted category of the training data. A target model of the target domain is trained based on the training data, the true label and the first label.

17 Claims, 6 Drawing Sheets

(51) Int. Cl.
*G06N 3/08* (2023.01)
*G16H 10/60* (2018.01)

(56) References Cited

U.S. PATENT DOCUMENTS

| | | | | |
|---|---|---|---|---|
| 2018/0240233 | A1* | 8/2018 | Kiraly | G06T 7/0012 |
| 2018/0268244 | A1* | 9/2018 | Moazzami | G06V 20/176 |
| 2019/0385019 | A1* | 12/2019 | Bazrafkan | G06N 7/00 |
| 2021/0034985 | A1* | 2/2021 | Vongkulbhisal | G06N 3/084 |
| 2021/0042667 | A1* | 2/2021 | Ghosh | G16H 50/70 |
| 2021/0089819 | A1* | 3/2021 | Tschiatschek | G06F 21/6245 |
| 2021/0209481 | A1* | 7/2021 | Moradi | G06F 11/3447 |
| 2021/0265018 | A1* | 8/2021 | Dutta | G16B 30/00 |
| 2021/0342544 | A1* | 11/2021 | Galle | G06N 5/04 |
| 2022/0051105 | A1* | 2/2022 | Fukuda | G10L 15/063 |
| 2023/0214715 | A1* | 7/2023 | Cheng | G06N 7/01 |
| | | | | 706/12 |

OTHER PUBLICATIONS

Ruder et al., "Knowledge Adaptation: Teaching to Adapt", Feb. 2107, pp. 1-11 (Year: 2017).*

Arteaga et al., "Knowledge Distillation for Semi-Supervised Domain Adaptation", ArXiv.com, Aug. 16, 2019, pp. 1-9 (Year: 2019).*

Asami et al., 'Domain Adaptation of DNN Acoustic Models using Knowledge Distillation, © 2017 IEEE, ICASSP 2017, 5 pages.

Asif et al., "Ensemble Knowledge Distillation for Learning Improved and Efficient Networks", IBM Research Austrailia, Sep. 17, 2019, 12 pages.

Mell et al., "The NIST Definition of Cloud Computing", Special Publication 800-145, National Institute of Standards and Technology, US. Department of Commerce, Sep. 2011, 7 pages.

Orbes-Arteainst et al., "Knowledge Distillation for Semi-supervised Domain Adaptation", © Springer Nature Switzerland AG 2019, L. Zhou et al. (Eds.): OR 2.0 2019/MLCN 2019, LNCS 11796, 9 pages, <https://link.springer.com/chapter/10.1007/978-3-030-32695-1_8>.

Ruder et al., "Knowledge Adaptation: Teaching to Adapt", Under review as a conference paper at ICLR 2017, 12 pages, <https://openreview.net/pdf?id=rJRhzzKxl>.

Shokri et al., "Membership Inference Attacks Against Machine Learning Models", arXiv:1610.05820v2 [cs.Cr] Mar. 31, 2017, 16 pages.

Wang et al., "Private Model Compression via Knowledge Distillation", Copyright c 2019, Association for the Advancement of Artificial Intelligence, 8 pages, <https://aaai.org/ojs/index.php/AAAI/article/view/3913>.

* cited by examiner

DOMAIN ADAPTATION

BACKGROUND

The present disclosure relates to machine learning, and more specifically, to a method, system and computer program product for domain adaptation.

Along with the accumulation of digital healthcare data, machine learning algorithms have been widely used to build numerous models to generate insights for disease prevention, diagnosis, treatments and prognosis. Some models within the machine learning space employ risk models. Risk models require widespread use in order to properly confirm their usability in the intended domains.

SUMMARY

According to one embodiment of the present disclosure, there is provided a computer-implemented method. The method comprises obtaining a source model of a source domain, wherein the source model is trained to generate a label indicating a predicted category of first data from the source domain. The method further comprises obtaining a training sample from a target domain, wherein the training sample comprises training data from the target domain and a true label indicating a true category of the training data from the target domain. The method further comprises generating a first label for the training data by using the source model, wherein the first label indicates a predicted category of the training data. The method further comprises training a target model of the target domain based on the training data, the true label and the first label, wherein the target model is trained to generate a label indicating a predicted category of second data from the target domain.

According to another embodiment of the present disclosure, there is provided a system. The system comprises a processing unit and a memory coupled to the processing unit. The memory stores instructions that, when executed by the processing unit, perform actions comprising: obtaining a source model of a source domain, wherein the source model is trained to generate a label indicating a predicted category of first data from the source domain; obtaining a training sample from a target domain, wherein the training sample comprises training data from the target domain and a true label indicating a true category of the training data from the target domain; generating a first label for the training data by using the source model, wherein the first label indicates a predicted category of the training data; and training a target model of the target domain based on the training data, the true label and the first label, wherein the target model is trained to generate a label indicating a predicted category of second data from the target domain.

According to yet another embodiment of the present disclosure, there is provided a computer program product. The computer program product is tangibly stored on non-transient machine-readable medium and comprises machine-executable instructions. The machine-executable instructions, when executed on a device, cause the device to perform acts comprising: obtaining a source model of a source domain, wherein the source model is trained to generate a label indicating a predicted category of first data from the source domain; obtaining a training sample from a target domain, wherein the training sample comprises training data from the target domain and a true label indicating a true category of the training data from the target domain; generating a first label for the training data by using the source model, wherein the first label indicates a predicted category of the training data; and training a target model of the target domain based on the training data, the true label and the first label, wherein the target model is trained to generate a label indicating a predicted category of second data from the target domain.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

Throughout the drawings, same or similar reference numerals represent the same or similar elements.

DETAILED DESCRIPTION

Figure 1:
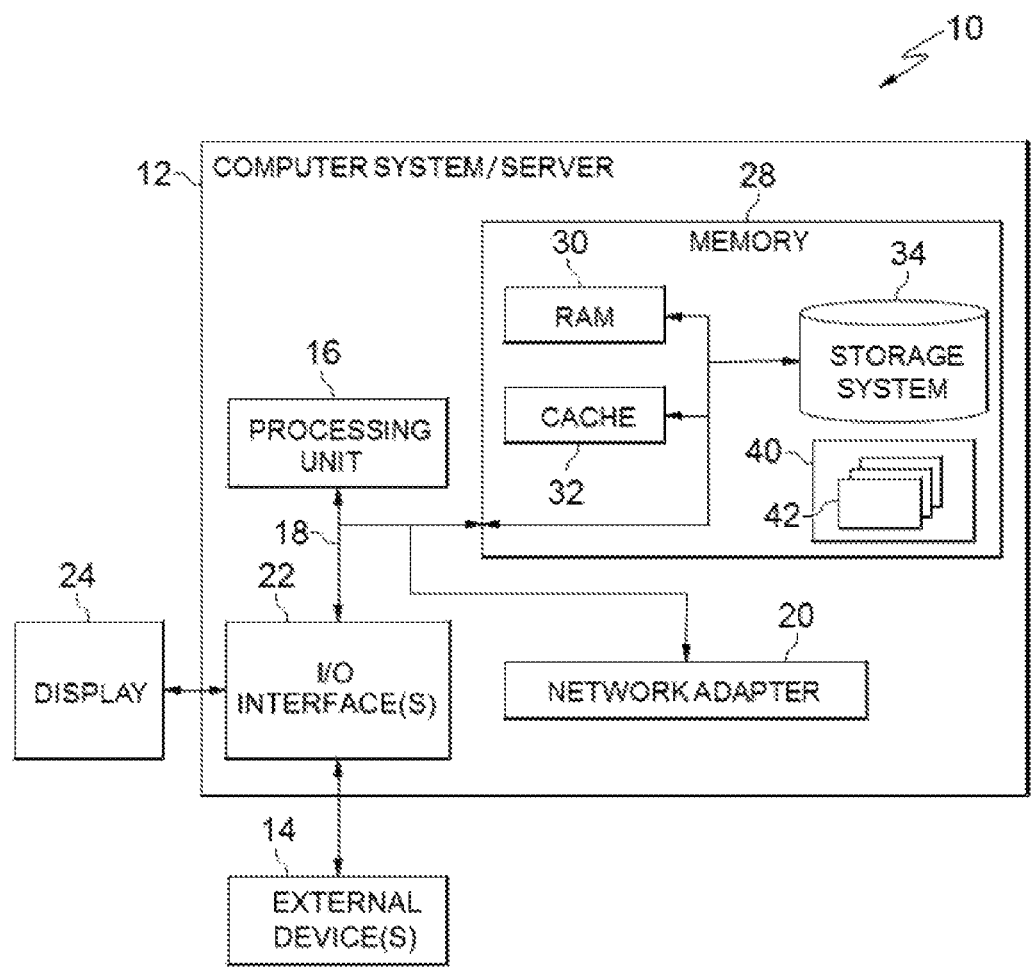
FIG. 1 depicts a cloud computing node according to an embodiment of the present disclosure.

When adapting a model from its original situation (also referred to as "source domain") to a new situation (also referred to as "target domain"), it becomes a challenge how to enhance the generalization ability. Embodiments of the present invention enable enhanced domain adaptation in machine learning environments.

Some embodiments will be described in more detail with reference to the accompanying drawings, in which the embodiments of the present disclosure have been illustrated. However, the present disclosure can be implemented in various manners, and thus should not be construed to be limited to the embodiments disclosed herein.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (Saas): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12 or a portable electronic device such as a communication device, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
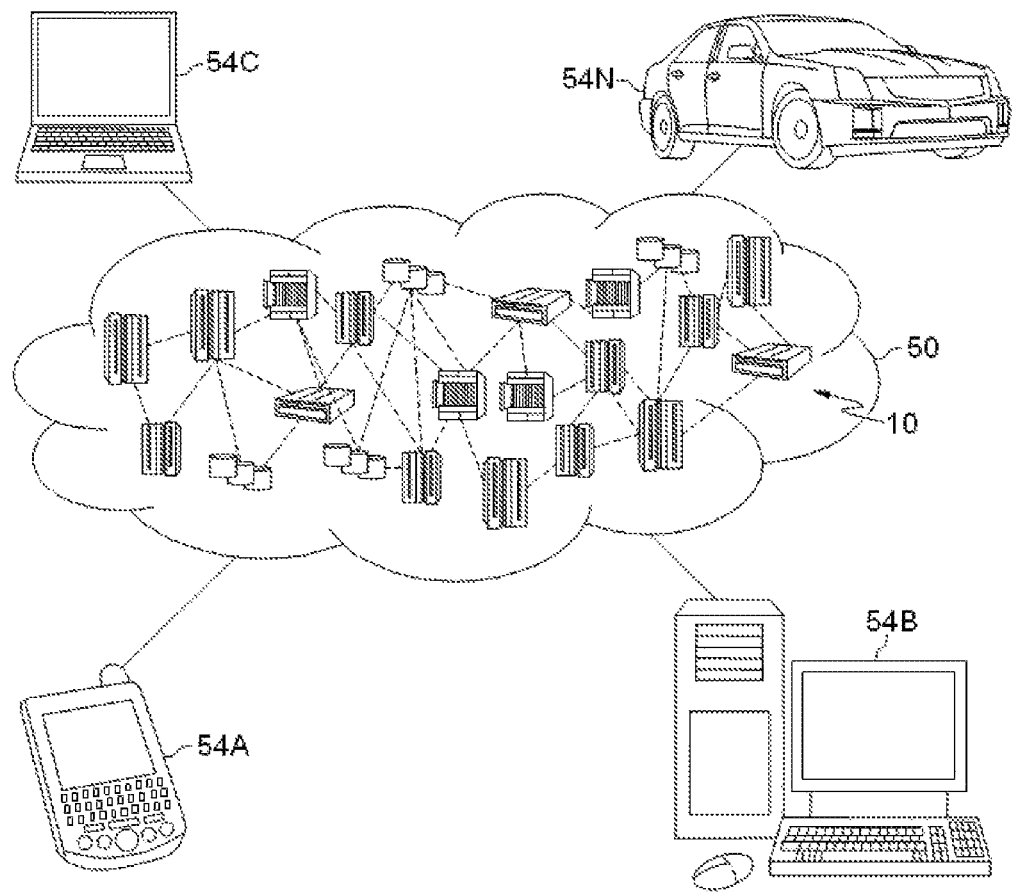
FIG. 2 depicts a cloud computing environment according to an embodiment of the present disclosure.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
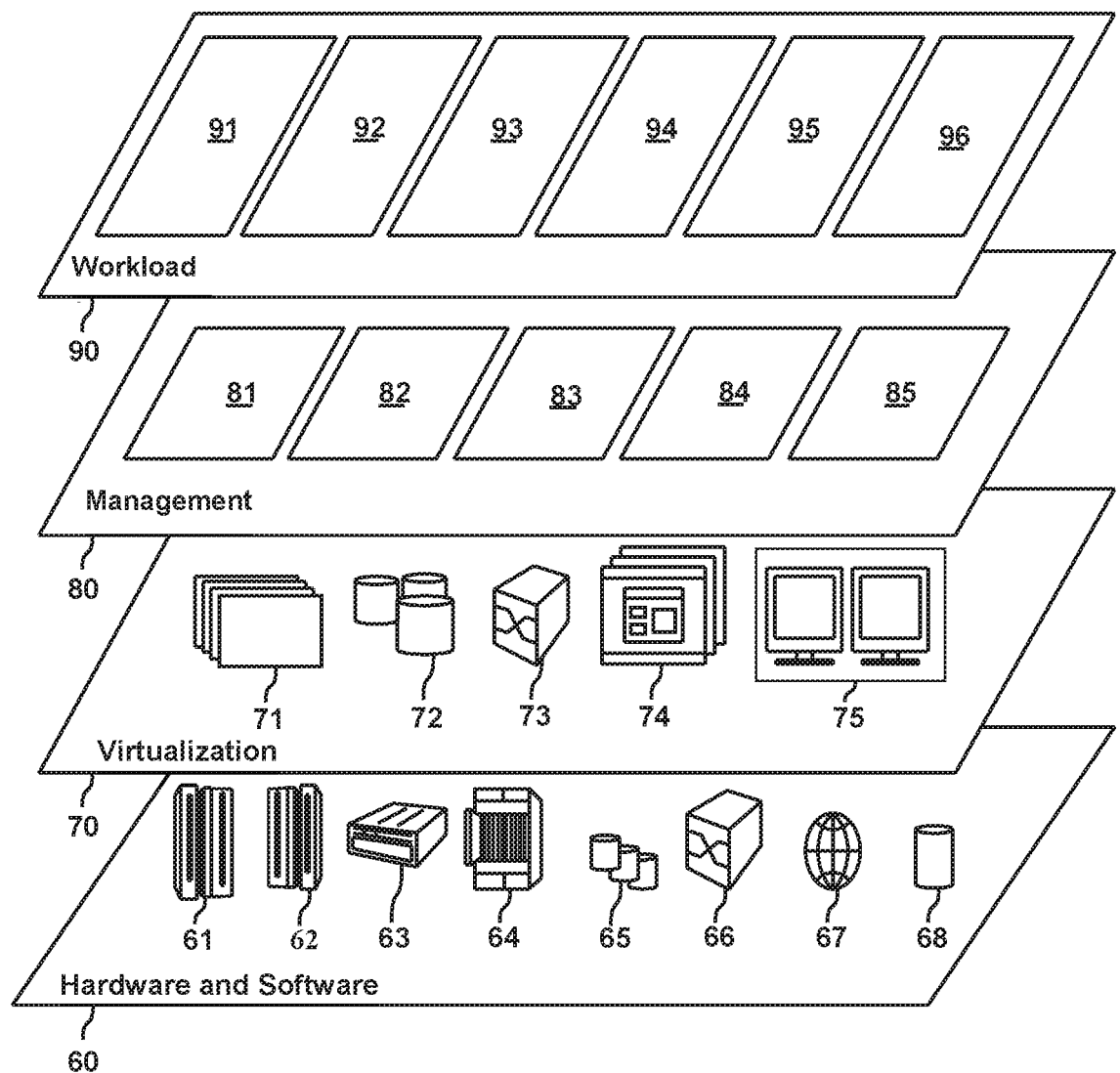
FIG. 3 depicts abstraction model layers according to an embodiment of the present disclosure.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and domain adaptation 96. Hereinafter, reference will be made to FIG. 4 to FIG. 6 to describe details of the domain adaptation 96.

As described above, along with the accumulation of digital healthcare data, machine learning algorithms have been widely used to build numerous models to generate insights for disease prevention, diagnosis, treatments and prognosis. While more and more models are used in the healthcare industry, however, sharing of healthcare datasets which were used to build these models is always highly restricted under most circumstances. When other healthcare institutes try to consume or apply such a model, it is often impossible for them to get the privilege of using the source healthcare dataset that was used to build the model during model adaptation. When adapting a model from a source domain to a target domain, it becomes a challenge how to enhance the generalization ability.

Some existing solutions use a knowledge distillation framework for model adaptation. In the knowledge distillation framework, a big model that achieves high accuracy but requires massive computation time is used as a teacher model. A small feasible model, called a student model, is trained to imitate the behavior of the teacher model by using output of the teacher model. As such, knowledge of the teacher model can be transferred to the student model. However, in these solutions, the teacher model and the student model usually target a same domain. For example, during model adaptation, the training dataset used to train the teacher model can be accessed and used to train the student model. When applying the knowledge distillation framework to domain adaptation, it is difficult to decide how much knowledge should be distilled from the teacher model.

In order to at least partially solve the above and other potential problems, embodiments of the present disclosure provide a solution for domain adaptation. According to embodiments of the present disclosure, a source model of a source domain is obtained, where the source model is trained to generate a label indicating a predicted category of first data from the source domain. A training sample from a target domain is obtained, where the training sample comprises training data from the target domain and a true label indicating a true category of the training data from the target domain. A first label is generated for the training data by using the source model. The first label indicates a predicted category of the training data. A target model of the target domain is trained based on the training data, the true label and the first label, where the target model is trained to generate a label indicating a predicted category of second data from the target domain.

In this way, knowledge of the source model trained for the source domain can be transferred to a target model trained for the target domain. The generalization ability can be enhanced even when the source domain and the target domain have different data distributions, the source domain data is absent and/or the target domain data is not sufficient. Embodiments of the present disclosure can be applied to scenarios where models are frequently adapted to new domains but the access of the source training data is restricted, such as, the healthcare scenario and the like. In the following, the healthcare scenario will be taken as an example to describe embodiments of the present disclosure. It is to be understood that this is merely for the purpose of illustration, without suggesting any limitations as to the scope of the present disclosure.

As used herein, the term "model" may refer to a machine learning model which can handle inputs and provide corresponding outputs. Examples of the model may include but not be limited to linear model, non-linear model, neutral network model and so on. Taking the neutral network model as an example, the neutral network model usually includes an input layer, an output layer and one or more hidden layers between the input and output layers. Individual layers of the neural network model are connected in sequence, such that an output of a preceding layer is provided as an input for a following layer, where the input layer receives the input of the neural network model while the output of the output layer acts as the final output of the neural network model. Each layer of the neural network model includes one or more nodes (also known as processing nodes or neurons) and each node processes the input from the preceding layer.

Figure 4:
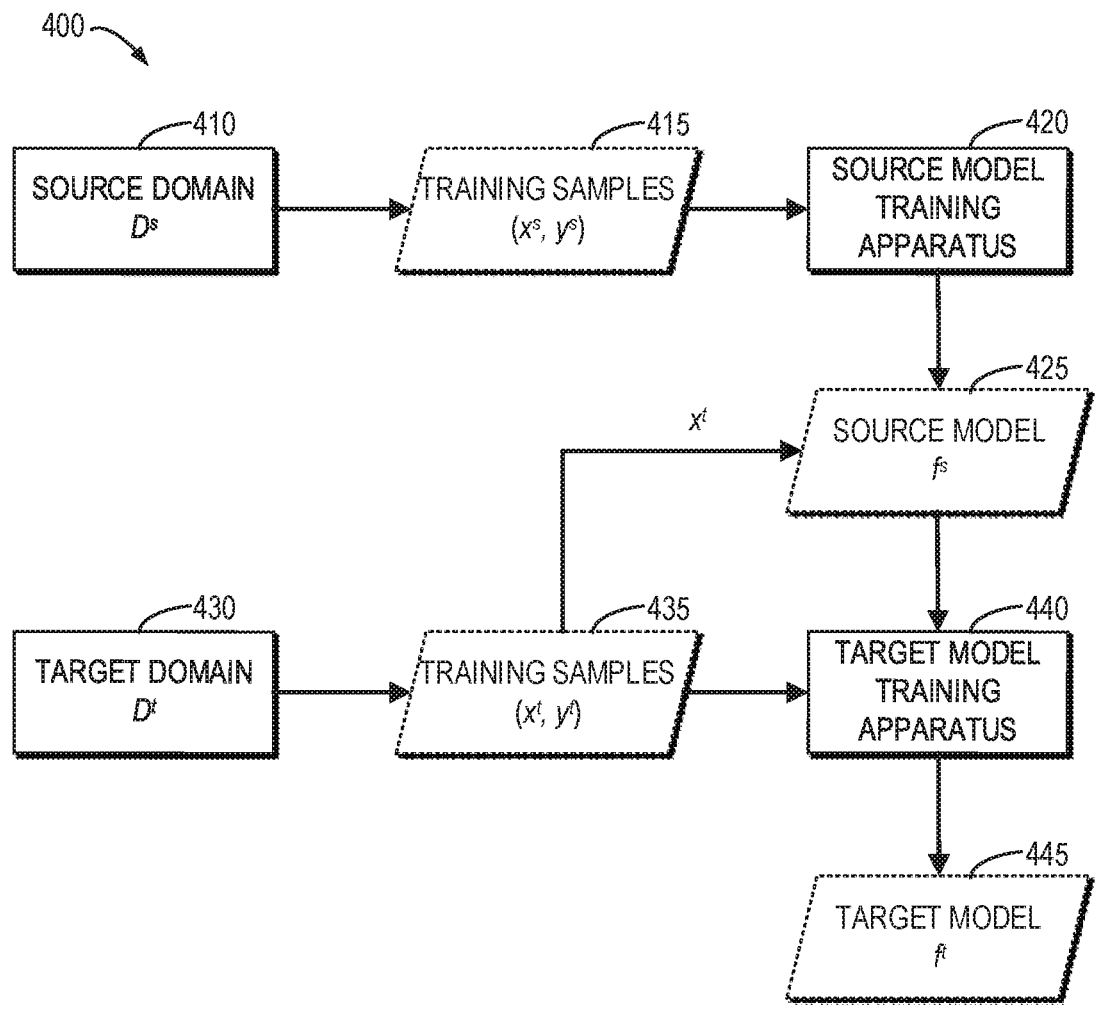
FIG. 4 depicts a system according to embodiments of the present disclosure.

With reference now to FIG. 4, a system 400 in which embodiments of the present disclosure can be implemented is shown. It is to be understood that the structure and functionality of the system 400 are described only for the purpose of illustration without suggesting any limitations as to the scope of the present disclosure. The embodiments of the present disclosure can be embodied with a different structure and/or functionality.

As shown in FIG. 4, the system 400 may generally comprise a source model training apparatus 420 and a target model training apparatus 440. In some embodiments, the source model training apparatus 420 and the target model training apparatus 440 can be implemented in different physical devices, respectively. Alternatively, in some embodiments, the source model training apparatus 420 and the target model training apparatus 440 can be implemented in a same physical device. For example, the source model training apparatus 420 and/or the target model training apparatus 440 may be implemented by computer system/server 12 of FIG. 1.

The source model training apparatus 420 may train a source model/425 based on training samples 415 from a source domain $D^s$ 410. Each training sample $(x^s, y^s)$ 415 may comprise training data $x^s$ from the source domain $D^s$ 410 and a true label $y^s$ indicating a true category of the training data $x^s$ from the source domain $D^s$ 410. The source model $f^s$ 425 may be trained to generate, for data from the source domain $D^s$ 410, a label indicating a predicted category of the data. For example, the source model $f^s$ 425 may be implemented as a neutral network model or any other suitable machine learning model.

In the healthcare scenario, for example, the source domain $D^s$ 410 may represent a first hospital and each training sample $(x^s, y^s)$ 415 may comprise healthcare data $x^s$ of a patient from the first hospital and a true label $y^s$ indicating a disease that the patient actually suffered from. The source model training apparatus 420 may train the source model $f^s$ 425 based on the training samples 415, such that the source model $f^s$ 425 can predict a disease for a patient (also referred to as "first patient") from the first hospital based on healthcare data of the first patient and generates a label indicating the predicted disease. It is to be understood that, any suitable machine learning algorithm or any suitable loss function can be used to train the source model f 425 and the scope of the present disclosure is not limited in this aspect.

The target model training apparatus 440 may train a target model/445 based on training samples 435 from a target domain $D^t$ 430 and by transferring knowledge from the source model $f^s$ 425 to the target model/445. Each training sample $(x^t, y^t)$ 435 may comprise training data $x^t$ from the target domain $D^t$ 430 and a true label $y^t$ indicating a true category of the training data from the target domain $D^t$ 430. The target model $f^t$ 445 may be trained to generate, for data from the target domain $D^t$ 430, a label indicating a predicted category of the data. For example, the target model $f^t$ 445 may be implemented as a liner classification model or any other suitable machine learning model.

In the healthcare scenario, for example, the target domain $D^t$ 430 may represent a second hospital and each training sample $(x^t, y^t)$ 435 may comprise healthcare data $x^t$ of a patient from the second hospital and a true label $y^t$ indicating a disease that the patient actually suffered from. In some cases, the second hospital and the first hospital may be far from each other (for example, they may locate in different countries) and thus the patient cohort from the first hospital may have significant different characters from the patient cohort from the second hospital. If the source model $f^s$ 425 is directly applied to the patient cohort from the second hospital, the predicted results (that is, the predicted diseases)

may not be accurate. Moreover, the second hospital may be a relatively new hospital, which may not be able to collect sufficient healthcare data of patients for model training, while the healthcare data from the first hospital which was used to train the source model f$^s$ 425 may be highly restricted and cannot be public to the second hospital. In this case, domain adaptation is essential to improve the generalization ability of the model.

As shown in FIG. 4, for each training sample (x$^t$, y$^t$) 435 from the target domain D$^t$ 430, the source model f$^s$ 425 may generate a label for the training data x$^t$. For example, the training data x$^t$ may indicate healthcare data x$^t$ of a patient from the second hospital and the label generated by the source model f$^s$ 425 may indicate a disease predicted by the source model f$^s$ 425 based on the healthcare data x$^t$ of the patient from the second hospital. The target model training apparatus 440 may train the target model/445 based on the training samples 435 from the target domain D$^t$ 430 and corresponding labels generated by the source model/425, such that the target model/445 can predict a disease for a patient (also referred to as "second patient") from the second hospital based on healthcare data of the second patient and generates a label indicating the predicted disease.

Figure 5:
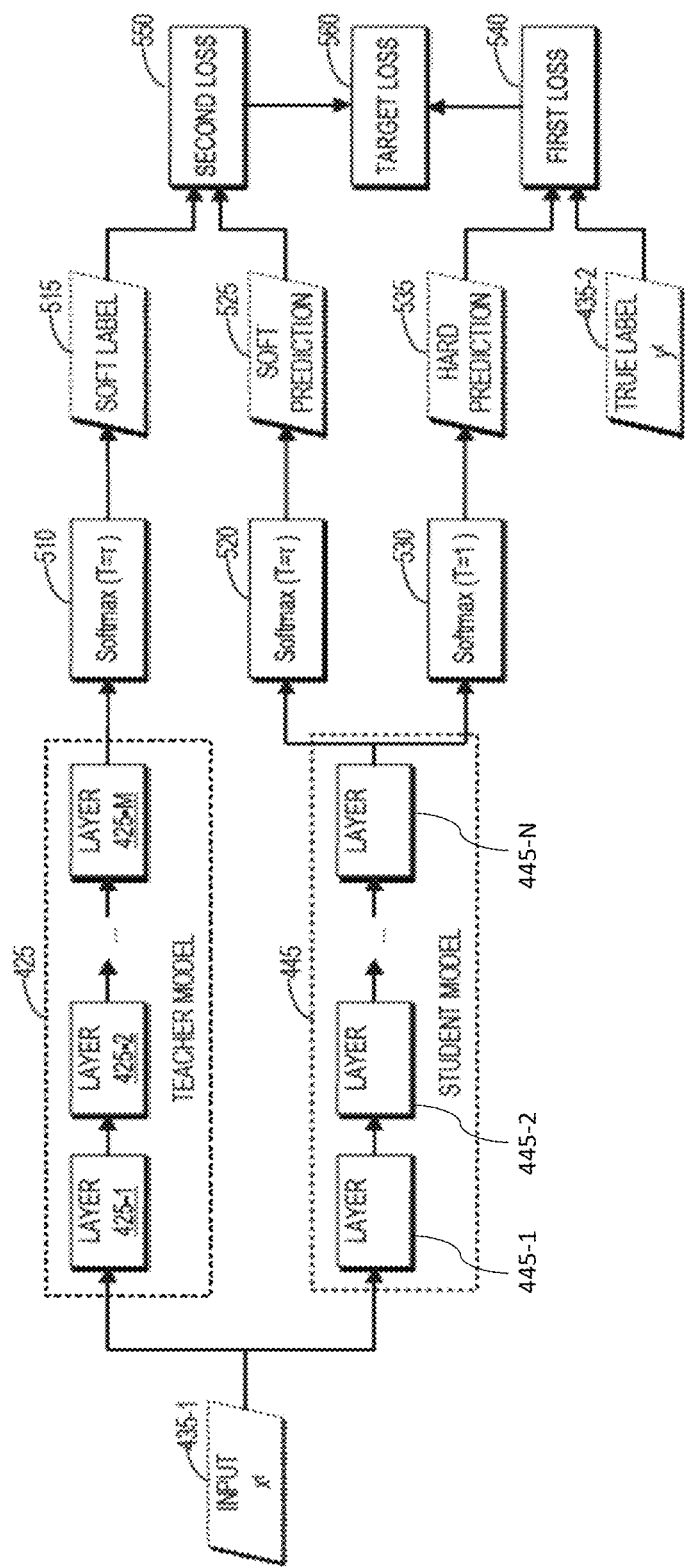
FIG. 5 depicts a schematic diagram for transferring knowledge from the source model to the target model according to embodiments of the present disclosure.

FIG. 5 depicts a schematic diagram for transferring knowledge from the source model to the target model according to embodiments of the present disclosure.

As shown in FIG. 5, the source model 425 may act as a teacher model, which comprises a plurality of layers 425-1, 425-2 . . . 425-M (where M>1). The target model 445 to be trained may act as a student model, which comprises a plurality of layers 445-1, 445-2 . . . 445-N (where N>1). As described above, each training sample (x$^t$, y$^t$) 435 may include training data x$^t$ 435-1 from the target domain D$^t$ 430 and a true label y$^t$ 435-2 indicating a true category of the training data x$^t$ 435-1. For example, the training data x$^t$ 435-1 represents healthcare data x$^t$ of a patient from the second hospital and the true label y$^t$ 435-2 indicates a disease that the patient actually suffered from.

As shown in FIG. 5, the training data x' 435-1 may be input to the source model 425. A softmax function 510 controlled by a predetermined temperature parameter T=t can be applied to an output of the last layer 425-M of the source model 425, so as to generate a soft label 515 (also referred to as "first soft label" in the following) for the training data x' 435-1. Moreover, the training data x' 435-1 may be input to the target model 445 that is to be trained. A softmax function 520 controlled by the predetermined temperature parameter T=τ can be applied to an output of the last layer 445-N of the target model 445, so as to generate a soft prediction 525 (also referred to as "second soft label" in the following) for the training data x' 435-1. Another softmax function 530 controlled by a temperature parameter T=1 can be applied to the output of the last layer 445-N of the target model 445, so as to generate a hard prediction 535 (also referred to as "hard label" in the following) for the training data x' 435-1.

In some embodiments, a first loss function 540 may be generated based on the hard label 535 and the true label 435-2, which measures a difference (also referred to as "first difference") between the hard label 535 and the true label 435-2. For example, the first loss function 540 may be a cross entropy loss function, which may be represented as: $L_1(\tilde{y}^t, y^t)$, where y$^t$ represents the true label 435-2, $\tilde{y}^t$ represents the hard label 535 and $L_1(\ )$ represents the cross entropy loss function.

In some embodiments, a second loss function 550 may be generated based on the first soft label 515 and the second soft label 525, which measures a difference (also referred to as "second difference") between the first soft label 515 and the second soft label 525. For example, the second loss function 550 may be a cross entropy loss function, which may be represented as: $L_2(6(z^t, \tau), 6(z^s, \tau))$, where z$^t$ represents the output of the last layer 445-M of the target model 445, z$^s$ represents the output of the last layer 425-M of the source model 425, τ represents the predetermined temperature parameter, $6(z^t, \tau)$ represents the first soft label 515, $6(z^s, \tau)$ represents the second soft label 525 and $L_2(\ )$ represents the cross entropy loss function.

As shown in FIG. 5, a target loss function 560 to be used for training the target model 445 can be determined based on the loss functions 540 and 550. For example, model parameters of the target model 445 may be iteratively updated, such that the target loss function 560 is minimized. In some embodiments, the target loss function 560 may be represented as below:

$$L=\lambda * L_1(\tilde{y}^t, y^t)+(1-\lambda)*L_2(6(z^s,\tau),6(z^s,\tau)) \quad (1)$$

where λ represents a dynamic weight applied to the loss function $L_1(\tilde{y}^t, y^t)$ and (1-λ) represents a weight applied to the loss function $L_2(6(z^t, \tau), 6(z^s, \tau))$.

In some embodiments, the dynamic weight λ may be determined as below:

$$\lambda=10+\delta * \mathbb{1}_{(y^t \neq 6(z^s))} \quad (2)$$

where do is a predetermined parameter and $0 \leq \lambda_0 \leq 1$; δ is a predetermined parameter and δ>0; $6(z^s)$ represents a label predicted by the source model 425, for example, by applying a softmax function controlled by a predetermined temperature parameter T=1 to the output of the last layer 425-M of the source model 425); and y$^t$ represents the true label 435-2. If $y^t \neq 6(z^s)$, $\mathbb{1}(y^t \neq 6(z\$))=1$; otherwise, $\mathbb{1}(y^t \neq 6(z^s))=0$. That is, if $6(z^s)$ matches y$^t$, the value of the weight λ will be close to 0 and the value of (1-λ) will be close to 1, which means that the target model 445 is to learn more knowledge from the source model 425. However, if $6(z^s)$ does not match y$^t$, the value of A will be close to 1 and the value of (1-λ) will be close to 0, which means that more attention will be put on the training samples 435 from the target domain D$^t$ 430 instead of knowledge from the source model 425. As such, the generalization ability of the target model 445 can be enhanced.

Figure 6:
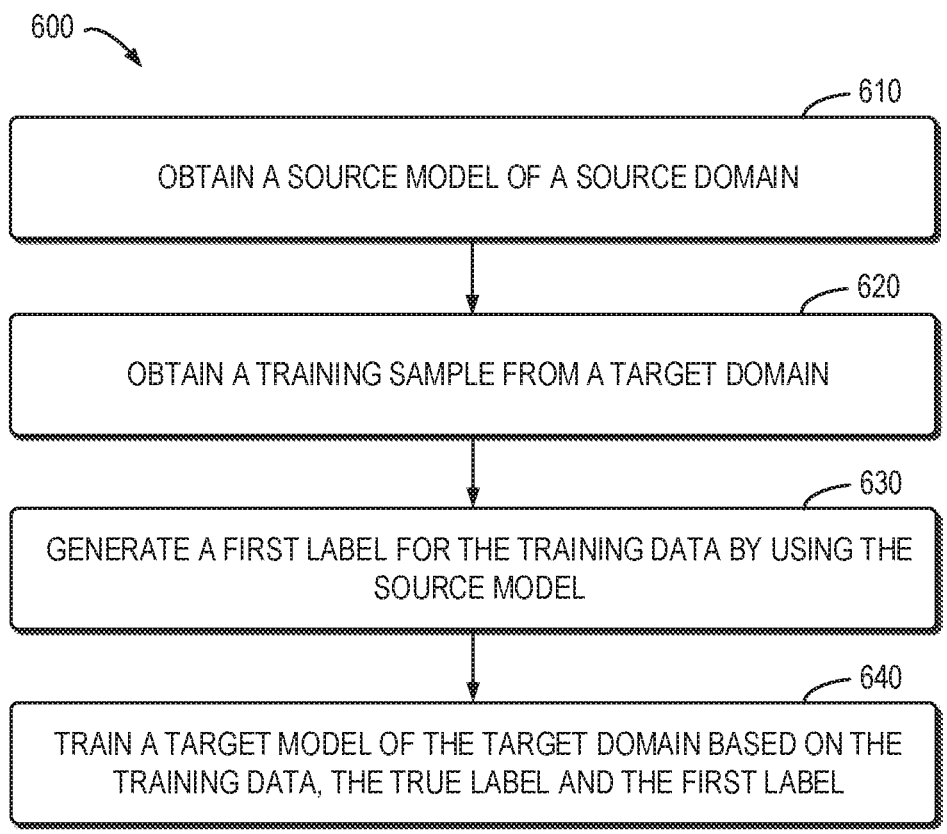
FIG. 6 depicts a flowchart of an example method for domain adaptation according to embodiments of the present disclosure.

FIG. 6 depicts a flowchart of an example method 600 for domain adaptation according to embodiments of the present disclosure. For example, the method 600 may be implemented by the system 400 as shown in FIG. 4. It is to be understood that the method 600 may also comprise additional blocks (not shown) and/or may omit the illustrated blocks. The scope of the present disclosure described herein is not limited in this aspect.

At block 610, the system 400 (for example, the target model training apparatus 440) obtains a source model 425 of a source domain 410. The source model 425 is trained to generate a label indicating a predicted category of first data from the source domain 410.

In some embodiments, the system 400 (for example, the source model training apparatus 420) may obtain a group of training samples 415 from the source domain 410, where each of the training samples 415 comprises training data from the source domain 410 and a true label indicating a true category of the training data. The system 400 (for example, the source model training apparatus 420) may train the source model 425 based on the group of training samples 415.

At block 620, the system 400 (for example, the target model training apparatus 440) obtains a training sample 435 from a target domain 430, where the training sample comprises training data 435-1 from the target domain 430 and a true label 435-2 indicating a true category of the training data from the target domain.

At block 630, the system 400 (for example, the target model training apparatus 440) generates a first label 515 for the training data 435-1 by using the source model 425. The first label 515 indicates a predicted category of the training data 435-1.

At block 640, the system 400 (for example, the target model training apparatus 440) trains a target model 445 of the target domain 430 based on the training data 435-1, the true label 435-2 and the first label 515 generated by the source model 425. The target model is trained to generate a label indicating a predicted category of second data from the target domain 430.

In some embodiments, the first label 515 is a first soft label generated by the source model 425. The system 400 (for example, the target model training apparatus 440) may generate a second soft label 525 and a hard label 535 for the training data by using the target model 445. The system 400 (for example, the target model training apparatus 440) may determine a loss function 560 based on a first difference between the hard label 535 and the true label 435-2 and a second difference between the first soft label 515 and the second soft label 525. The system 400 (for example, the target model training apparatus 440) may train the target model 445 by minimizing the loss function 560.

In some embodiments, in order to determine the loss function 560, the first difference may be weighted based on a first weight $\lambda$ and the second difference may be weighted based on a second weight $(1-\lambda)$. The system 400 (for example, the target model training apparatus 440) may determine the loss function 560 by summing the weighed first difference and the weighted second difference.

In some embodiments, in response to the first label matching the true label, the system 400 (for example, the target model training apparatus 440) may decrease the first weight $\lambda$ and increase the second weight $(1-\lambda)$. In some embodiments, in response to the first label not matching the true label, the system 400 (for example, the target model training apparatus 440) may increase the first weight $\lambda$ and decrease the second weight $(1-\lambda)$.

It can be seen that, according to embodiments of the present disclosure provide a solution for domain adaptation. According to embodiments of the present disclosure, a source model of a source domain is obtained, where the source model is trained to generate a label indicating a predicted category of first data from the source domain. A training sample from a target domain is obtained, where the training sample comprises training data from the target domain and a true label indicating a true category of the training data from the target domain. A first label is generated for the training data by using the source model. The first label indicates a predicted category of the training data. A target model of the target domain is trained based on the training data, the true label and the first label, where the target model is trained to generate a label indicating a predicted category of second data from the target domain.

In this way, knowledge of the source model trained for the source domain can be transferred to a target model trained for the target domain. The generalization ability can be enhanced even when the source domain and the target domain have different data distributions, the source domain data is absent and/or the target domain data is not sufficient. Embodiments of the present disclosure can be applied to scenarios where models are frequently adapted to new domains but the access of the source training data is restricted.

It should be noted that the domain adaptation according to embodiments of this disclosure could be implemented by computer system/server 12 of FIG. 1.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   obtaining, by one or more processors, a source model of a source domain, wherein the source model is trained to predict at least one first category of first data from the source domain;
   obtaining, by the one or more processors, a target training sample from a target domain, wherein the target training sample comprises target training data from the target domain and a target true label indicating a target true category of the target training data;
   generating, by the one or more processors, a first label for the target training data by using the source model, wherein the first label indicates a predicted category of the target training data, wherein the first label is a first soft label generated by the source model;
   training, by the one or more processors, a target model of the target domain based on the target training data, the target true label, the first label, and a plurality of weights associated with the target true label and the first label, wherein the target model is trained to predict at least one second category of second data from the target domain, wherein training the target model comprises:
   generating, by the one or more processors, a second soft label and a hard label for the target training data by using the target model;
   determining, by the one or more processors, a loss function based on a first difference between the hard label and the target true label and a second difference between the first soft label and the second soft label labels; and
   training, by one or more processors, the target model by minimizing the loss function.

2. The method of claim 1, wherein obtaining the source model comprises:
   obtaining, by the one or more processors, a group of source training samples from the source domain, wherein the group of source training samples comprises source training data from the source domain and a source true label indicating a source true category of the source training data from the source domain; and
   training, by the one or more processors, the source model based on the group of source training samples.

3. The method of claim 1, wherein determining the loss function comprises:
   weighting, by the one or more processors, the first difference based on a first weight and the second difference based on a second weight; and
   determining, by the one or more processors, the loss function by summing the weighted first difference and the weighted second difference.

4. The method of claim 3, further comprising:
in response to the first label matching the target true label, decreasing, by the one or more processors, the first weight while increasing the second weight.

5. The method of claim 3, further comprising:
in response to the first label not matching the target true label, increasing, by the one or more processors, the first weight while decreasing the second weight.

6. The method of claim 1, wherein the first data is first healthcare data of a first patient from a first hospital and the source model is trained to predict the at least one first category indicating a first predicted disease of the first patient, and where in the second data is second healthcare data of a second patient from a second hospital and the target model is trained to predict the at least one second category indicating a second predicted disease of the second patient.

7. A system comprising:
a processing unit; and
a memory coupled to the processing unit and storing instructions thereon, the instructions, when executed by the processing unit, performing actions comprising:
obtaining, by one or more processors, a source model of a source domain, wherein the source model is trained to predict at least one first category of first data from the source domain;
obtaining, by the one or more processors, a target training sample from a target domain, wherein the target training sample comprises target training data from the target domain and a target true label indicating a target true category of the target training data;
generating, by the one or more processors, a first label for the target training data by using the source model, wherein the first label indicates a predicted category of the target training data, wherein the first label is a first soft label generated by the source model;
training, by the one or more processors, a target model of the target domain based on the target training data, the target true label, the first label, and a plurality of weights associated with the target true label and the first label, wherein the target model is trained to predict at least one second category of second data from the target domain, wherein training the target model comprises:
generating, by the one or more processors, a second soft label and a hard label for the target training data by using the target model;
determining, by the one or more processors, a loss function based on a first difference between the hard label and the target true label and a second difference between the first soft label and the second soft label labels; and
training, by one or more processors, the target model by minimizing the loss function.

8. The system of claim 7, wherein obtaining the source model comprises:
obtaining a group of source training samples from the source domain, wherein each of the group of source training samples comprises source training data from the source domain and a source true label indicating a source true category of the source training data from the source domain; and
training the source model based on the group of source training samples.

9. The system of claim 7, wherein determining the loss function comprises:
weighting the first difference based on a first weight and the second difference based on a second weight; and
determining the loss function by summing the weighted first difference and the weighted second difference.

10. The system of claim 9, wherein the actions further comprise:
in response to the first label matching the target true label, decreasing the first weight while increasing the second weight.

11. The system of claim 9, wherein the actions further comprise:
in response to the first label not matching the target true label, increasing the first weight while decreasing the second weight.

12. The system of claim 7, wherein the first data is first healthcare data of a first patient from a first hospital and the source model is trained to predict the at least one first category indicating a first predicted disease of the first patient, and where in the second data is second healthcare data of a second patient from a second hospital and the target model is trained to predict at least one second category indicating a second predicted disease of the second patient.

13. A computer program product being tangibly stored on a non-transient non-transitory machine-readable medium and comprising machine-executable instructions, the instructions, when executed on a device, causing the device to perform actions comprising:
obtaining, by one or more processors, a source model of a source domain, wherein the source model is trained to predict at least one first category of first data from the source domain;
obtaining, by the one or more processors, a target training sample from a target domain, wherein the target training sample comprises target training data from the target domain and a target true label indicating a target true category of the target training data;
generating, by the one or more processors, a first label for the target training data by using the source model, wherein the first label indicates a predicted category of the target training data, wherein the first label is a first soft label generated by the source model;
training, by the one or more processors, a target model of the target domain based on the target training data, the target true label, the first label, and a plurality of weights associated with the target true label and the first label, wherein the target model is trained to predict at least one second category of second data from the target domain, wherein training the target model comprises:
generating, by the one or more processors, a second soft label and a hard label for the target training data by using the target model;
determining, by the one or more processors, a loss function based on a first difference between the hard label and the target true label and a second difference between the first soft label and the second soft label labels; and
training, by one or more processors, the target model by minimizing the loss function.

14. The computer program product of claim 13, wherein obtaining the source model comprises:
obtaining a group of source training samples from the source domain, wherein each of the group of source training samples comprises source training data from the source domain and a source true label indicating a source true category of the source training data from the source domain; and
training, by one or more processors, the source model based on the group of source training samples.

15. The computer program product of claim 13, wherein determining the loss function comprises:
 weighting the first difference based on a first weight and the second difference based on a second weight; and
 determining the loss function by summing the weighted first difference and the weighted second difference.

16. The computer program product of claim 15, wherein the actions further comprise:
 in response to the first label matching the target true label, decreasing the first weight while increasing the second weight.

17. The computer program product of claim 15, wherein the actions further comprise:
 in response to the first label not matching the target true label, increasing the first weight while decreasing the second weight.

\* \* \* \* \*